(12) United States Patent
Mimura

(10) Patent No.: US 6,487,444 B2
(45) Date of Patent: Nov. 26, 2002

(54) DESIGN EVALUATION METHOD, EQUIPMENT THEREOF, AND GOODS DESIGN METHOD

(76) Inventor: Kenji Mimura, 29-1105, Wakabadai 4-chome, Asahi-ku, Yokohama-shi, Kanagawa, 241-0801 (JP)

( * ) Notice: Subject to any disclaimer, the term of this patent is extended or adjusted under 35 U.S.C. 154(b) by 40 days.

(21) Appl. No.: 09/791,851

(22) Filed: Feb. 26, 2001

(65) Prior Publication Data

US 2001/0029341 A1 Oct. 11, 2001

(30) Foreign Application Priority Data

Mar. 28, 2000 (JP) .......................... 2000-088230
Dec. 7, 2000 (JP) .......................... 2000-373361

(51) Int. Cl.$^7$ ................................. A61B 5/00
(52) U.S. Cl. ...................... 600/544; 600/300
(58) Field of Search ................. 600/300, 301, 600/544, 545, 558

(56) References Cited

U.S. PATENT DOCUMENTS

| | | | | |
|---|---|---|---|---|
| 5,243,517 A | * | 9/1993 | Schmidt et al. | 600/544 |
| 5,762,611 A | * | 6/1998 | Lewis et al. | 600/544 |
| 4,789,235 A | * | 12/1998 | Borah et al. | 600/544 |
| 5,983,129 A | * | 11/1999 | Cowan et al. | 600/544 |
| 6,292,688 B1 | * | 9/2001 | Patton | 600/544 |

* cited by examiner

Primary Examiner—Robert L. Nasser
(74) Attorney, Agent, or Firm—Lowe Hauptman Gilman & Berner, LLP

(57) ABSTRACT

The present inventions relates to a design evaluation method, equipment thereof, and a goods design method that make it possible to obtain a highly reliable evaluation of a design quality of an evaluated object. Thus, in the present invention, the design of an evaluated object is evaluated on the basis of a brain wave reaction by outputting an image, which expresses the design of the evaluated object, by image output means, and measuring brain waves of an arbitrary test subject by showing this image to the test subject. Hence, it is possible to obtain a highly reliable evaluation result without any subjective judgment based on the knowledge and experience of the test subject.

11 Claims, 4 Drawing Sheets

DESIGN EVALUATION METHOD, EQUIPMENT THEREOF, AND GOODS DESIGN METHOD

Background of the Invention

1. Field of the Invention

The present invention relates to a design evaluation method, equipment thereof, and a goods design method for obtaining the evaluation about quality of designing goods on the occasion of manufacturing various types of products such as automobiles or the like.

2. Description of the Related Art

Generally, the design of industrial products or the like becomes one of important elements influencing the sales of goods in addition to the essential performance of the products. In particular, since the design according to the appearance of automobiles variously changes by consumers, liking, fashion, or the like, in a development phase before reaching a design and manufacturing phase, enough investigation is demanded in the decision of the design. Then, conventionally, the final design is decided on the basis of the evaluation that is reported by word of mouth or in writing by an estimator observing a design where product design is drawn.

However, the evaluation for the design is not highly reliable data since the evaluation does not always coincide with intuitive impression because subjective judgment based on the estimator's knowledge and experience is added to visual impression.

In addition, actually, when a consumer purchases a product, it is common that the consumer is given an incentive to purchase the product by looking at a photograph of a real object of the product displayed in an advertisement, on a catalog, or the like, or touching goods exhibited in a store. However, in a development phase where a real object of the product does not exist, only the evaluation for the design can be obtained, and furthermore there are many cases that the visual impression of the design and real object is different from each other.

Therefore, in any case, there is a case of resulting in that it could not be convinced in the development phase that the products would be largely sold by the design, and sales that were expected at the time of design decision are not realized in real sale.

SUMMARY OF THE INVENTION

A design evaluation method of the present invention includes the steps of outputting an image, where the design of an evaluated object is expressed, by predetermined image output means, measuring brain waves of an arbitrary test subject while showing this image to the test subject, and evaluating the design of the evaluated object on the basis of brain wave reactions.

Thereby, since the design of the evaluated object is evaluated on the basis of the brain wave reaction of the test subject who looks at the image, it is possible to obtain an intuitive evaluation result without any subjective judgement based on the knowledge and experience of the test subject.

In this case, by comparing a pattern of a local distribution condition of a brain wave electric potential on a test subject's scalp with a plural kind of reference patterns set beforehand, and judging which of the reference patterns is similar to the pattern of the brain wave electric potential measured, it is possible to measure the brain wave reaction more concretely on the basis of a characteristic of each reference pattern, for example, anger, joy, sorrow, or the like. In addition, by evaluating the design on the basis of the brain wave reactions of the test subject in a predetermined scene of the image, it becomes possible to measure an arbitrary scene where, for example, a reaction being important in evaluation is forecasted.

Moreover, by using images including scenes that show the evaluated object from different angles, for example, in the case that the evaluated object is an automobile, scenes, where the automobile is displayed from different angles such as the front and the side, or the like, and so on are expressed by the images.

In addition, by using images including the scenes which represent dynamic changes of the evaluated object, for example, if the evaluated object is an automobile, it is possible to express scenes or the like that generate dynamic changes such as a driving state of the automobile or an operating state of a moving part is expressed by images.

Moreover, by using images including scenes where represent the evaluated object with predetermined backgrounds, for example, if the evaluated object is an automobile, scenes or the like, that include different backgrounds such as a town area, a mountainous area, a daytime scene, a night scene, and each weather scene, are expressed by images.

In addition, by using images including scenes where an evaluated object is expressed with other articles or persons, for example, if the evaluated object is an automobile, scenes include other articles such as accessories, and embarkation, or persons such as a driver and a passenger are expressed by images.

Moreover, by producing the images by using computer graphics, it becomes possible to arbitrarily express the design of the evaluated object by the computer graphics.

Furthermore, by expressing an evaluated object, whose real object does not exist, in the image, the evaluated object whose real object does not exist is virtually expressed by the computer graphics.

In addition, by making the evaluated object be a vehicle, for example, the design of the vehicle such as an automobile or a motorcycle where appearance design is regarded as important is evaluated.

Moreover, in a goods design method of the present invention, the final design of goods can be decided on the basis of a highly reliable evaluation result before shifting to a design and manufacturing phase of the goods by using this design evaluation method. It, therefore, becomes possible to produce the goods having high probability of obtaining good sales, and hence, it is possible to contribute to the increase of sellers' profits.

DESCRIPTION OF THE PREFERRED EMBODIMENTS

Figure 1:
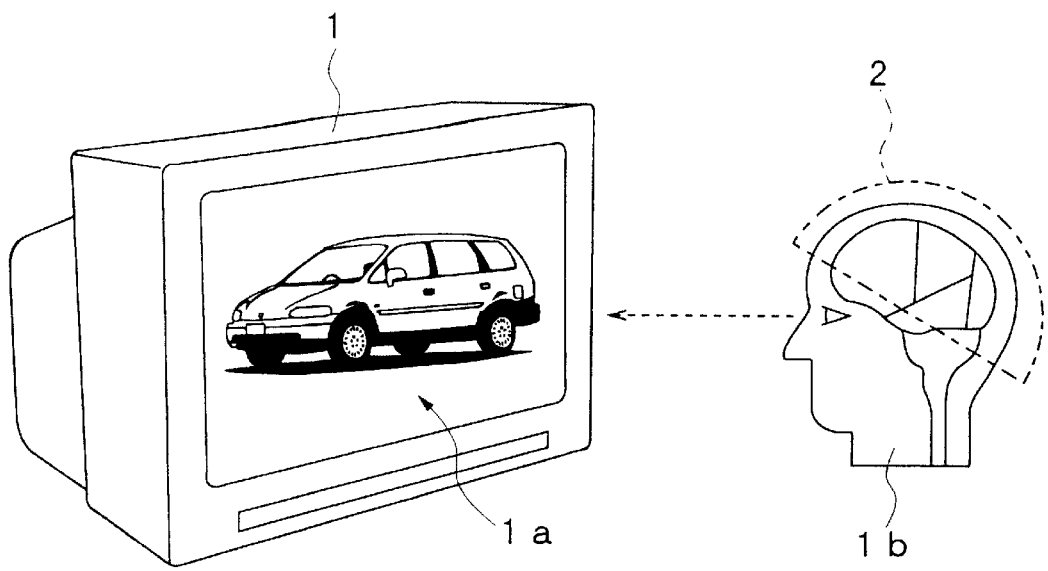
FIG. 1 is a schematic diagram of design evaluation equipment showing an embodiment of the present invention.
Figure 2:
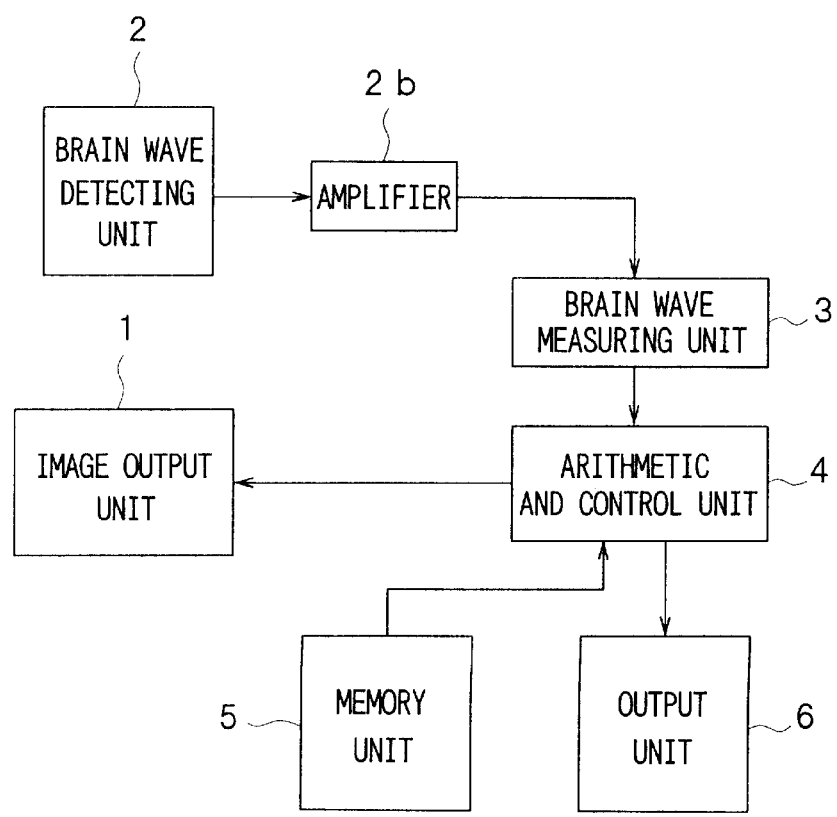
FIG. 2 is a block diagram showing a control system.

FIGS. 1 to 6 show an embodiment of the present invention.

Design evaluation equipment of this embodiment comprises: an image output unit 1 for outputting a predetermined image 1*a*; a brain wave detecting unit 2 for detecting brain waves of a test subject 1*b* who watches the image output unit 1; a brain wave measuring unit 3 for measuring an electric potential signal of a brain wave in time sequence with a detecting signal of the brain wave detecting unit 2; an arithmetic and control unit 4 for performing the analysis of brain wave data on the basis of measurement results of brain wave measuring unit 3, the control of the image output unit, and so on; a memory unit 5 for storing reference data for comparison with measured data; and an output unit 6 for outputting an evaluation result.

The image output unit 1 has a function of replaying an image recorded in, for example, a magnetic tape, and, for example, an image 1*a* where the design of an automobile is expressed is recorded. In this case, the data of the image 1*a* is not an image obtained by directly taking a picture of a real object, but is virtually produced with using computer graphics or the like.

The brain wave detecting unit 2 comprises well-known devices that are used for, for example, medical applications, and has a lot of electrodes 2*a* fixed on a scalp of a test subject 1*b*. Respective electrodes 2*a* of the brain wave detecting unit 2 are attached so as to scatter on many places of the scalp, and are connected to the brain wave measuring unit 3 through respective amplifiers 2*b*.

The brain wave measuring unit 3 comprises well-known devices digitalizing a detecting signal of the brain wave detecting unit 2, and is connected to the arithmetic and control unit 4. In this case, the brain wave measuring unit 3 is made to measure electric potentials on the scalp in positions of respective electrodes 2*a* of the brain wave detecting unit 2 simultaneously.

The arithmetic and control unit 4 is composed of a microcomputer, and is connected to the image output unit 1, memory unit 5 and output unit 6 respectively. Thus, the arithmetic and control unit 4 digitalizes quantity of character corresponding to each pattern from correlation patterns of the brain wave vs. electric potential on the scalp distribution measured by the brain wave measuring unit 3, and compares the quantity of character with reference data stored beforehand in the memory unit 5.

The memory unit 5 stores various reference data for comparison with the correlation pattern of the brain wave vs. electric potential on the scalp distribution, and each reference data is arbitrarily rewritable.

The output unit 6 comprises, for example, a display, a printer, or the like of a personal computer, and outputs a list of evaluation results.

Figure 3:
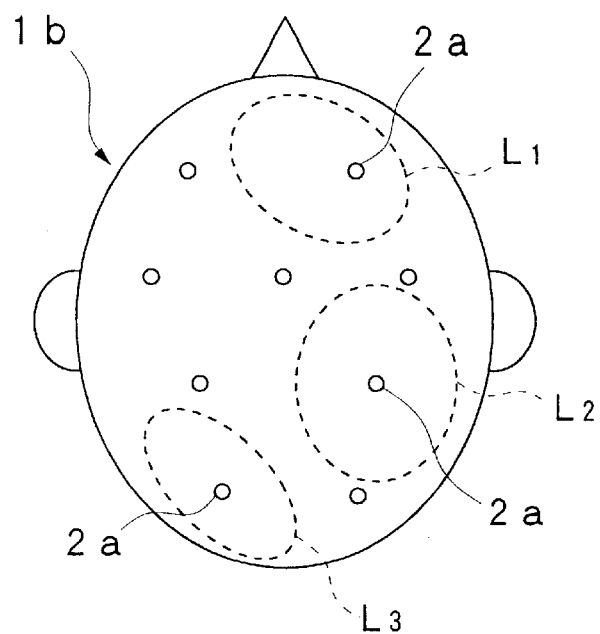
FIG. 3 is a schematic top view of a head showing a distribution of an electric potential on a scalp.

Here, the electroencephalography(EEG) analysis used for a design evaluation method of this embodiment will be described. In general, a human brain reacts by a given stimulation, and a brain wave changes depending on this. Nevertheless, it is considered that functions of a brain are localized, and it is made to be cleared by documents that electric potential distribution peculiar to each of participating and not-participating locations (for example, different locations L1, L2, and L3 on a scalp that are shown in FIG. 3) is formed because of conditions of emotion such as anger, joy, and sorrow. Then, in the present inventions, by measuring a positional distribution status (a pattern) that brain waves make on a scalp, comparing the distribution status with reference pattern of a plurality of emotion (anger, joy, sorrow, or the like) obtained beforehand by experiments and studies, and judging which of reference patterns has a characteristic similar to measured data, design is evaluated on the basis of emotion produced by stimulation which the test subject, looking at the design of an evaluated object, visually receives.

Figure 5:
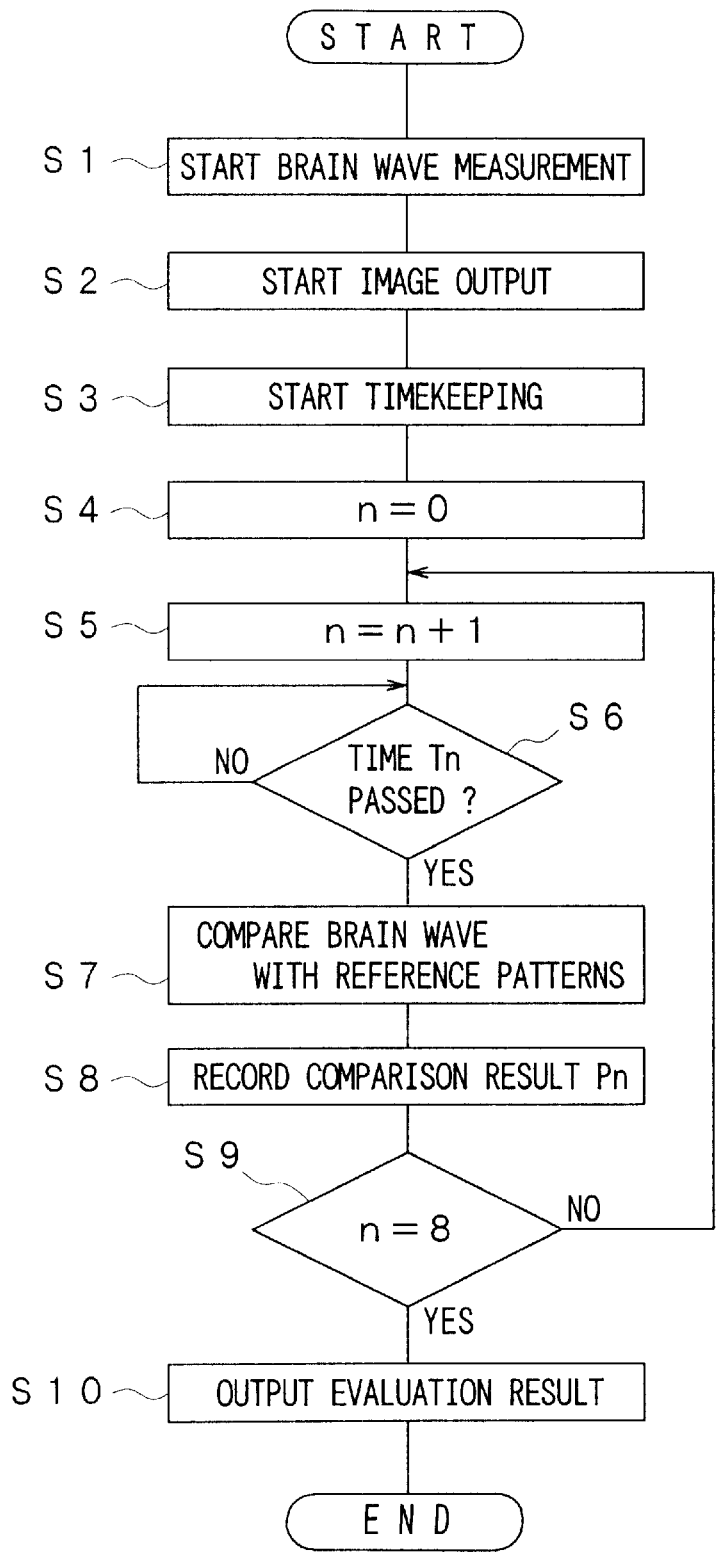
FIG. 5 is a flow chart showing an operation of an arithmetic and control unit.

Next, the operation of the arithmetic and control unit 4 in the design evaluation method according to this embodiment will be described with reference to a flow chart shown in FIG. 5.

Figure 4:
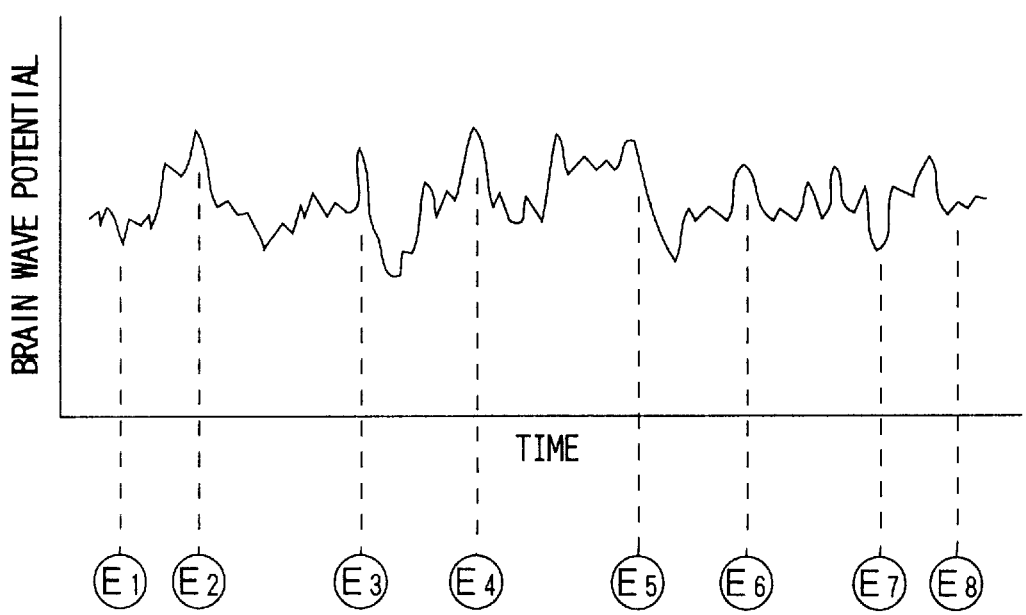
FIG. 4 is a chart showing changes of a brain wave in an arbitrary electrode position.

First, the arithmetic and control unit 4 starts the measurement of brain waves of the test subject 1*b* who observes the image output unit 1 (S1), outputs a predetermined image 1*a* to the image output unit 1 (S2), and starts timekeeping (S3). In this case, the image 1*a* can be dynamic images obtained by the evaluated object (for example, design of an automobile) being continuously displayed, or can be images obtained by sequentially switching static images. In addition, in the image 1a, a plurality of scenes (E1, E2, . . . , En), for which reactions of brain waves of the test subject 1*b* should be measured, is set in time sequence as shown in FIG. 4, and each scene appears when predetermined time (T1, T2, . . . , Tn) each passes since the start of the timekeeping. As respective scenes, for example, if an evaluated object is an automobile, scenes to be set are scenes where only the evaluated object is expressed or various kinds of scenes, for which the reaction important in evaluation is expected, in addition to scenes, where only one aspect is expressed, such as scenes where the automobile is displayed from various angles such as the front, and the side, a scene where dynamic changes such as a driving status of the automobile and an operation status of moving parts occur, scenes whose backgrounds such as a town area, a mountainous area, a daytime scene, a night scene, and each weather are varied, scenes where other articles such as accessories, and embarkation, or persons such as a driver and a passenger are expressed with the automobile. Next, after letting a variable n in the scene be zero (S4), 1 is added to n (S5), and if time Tn passes, a positional distribution status that brain waves at that time makes on a scalp (hereinafter, a brain wave electric potential pattern) is compared with each reference pattern (a plurality of sensitivity such as anger, joy, and sorrow) in the memory unit 5 (S7). Then, the most similar reference pattern is recorded as a comparison result Pn (S8). For example, if a brain wave electric potential pattern is the most similar to a reference pattern corresponding to the sensitivity of "joy" in a scene where an automobile is displayed from the front, the reference pattern of "joy" is recorded for the scene. Next, if the variable n does not reach a variable N in a final scene (S9), operation at the steps S5 to S8 is repeated and each scene (E1, E2, . . . , En) is evaluated. After that, if the variable n reaches the variable N in the final scene in the step S9, an evaluation result of each scene (E1, E2, . . . , En) is outputted by the output unit 6 (S10), and a program is finished.

By the evaluation results obtained as described above, for example, if the test subject 1*b* shows an reaction of producing the sensitivity of "joy" in the scene where the automobile is displayed from the front, it is possible to decide that the front design of the automobile gives the test subject 1*b* good impression. In addition, for example, if showing a reaction of producing the sensitivity of "anger" or "sorrow" in the scene where the automobile is driven in a town area, it is possible to judge that the design of the automobile does not match with a town area.

In this manner, according to the design evaluation method of the present invention, by outputting the image 1a, where the design of an evaluated object is expressed, by the above described image output unit 1, and measuring brain waves of the arbitrary test subject 1b while showing this image 1a to the test subject 1b, the design of the evaluated object is evaluated on the basis of brain wave reactions. Hence, it is possible to obtain a highly reliable evaluation result without any subjective judgment based on the knowledge and experience of the test subject 1b.

Figure 6:
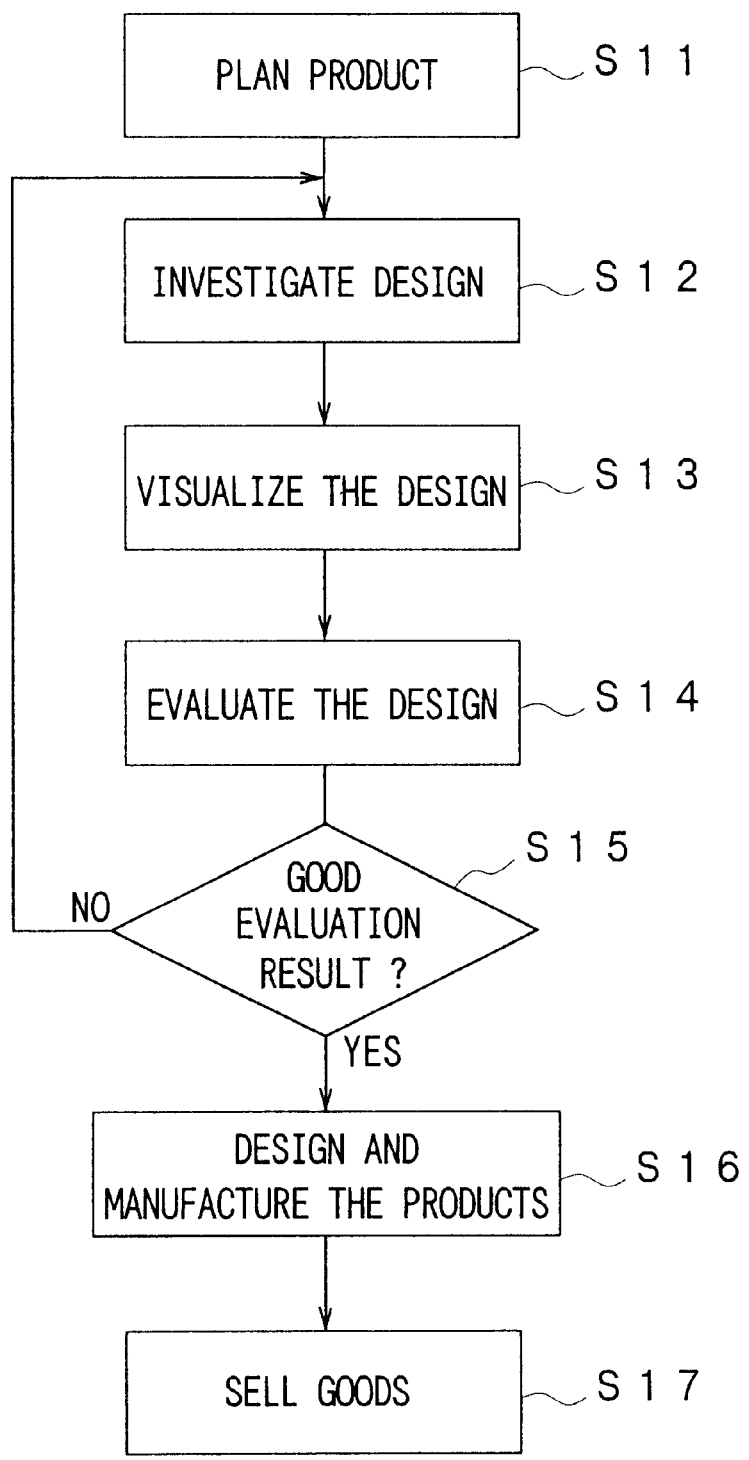
FIG. 6 is a flow chart showing a process from a goods-planning phase to a design and manufacturing phase.

Next, a goods design method using the design evaluation method will be explained. Thus, through a stage of goods planning as shown in FIG. 6 (S11), the initial goods design is concretely investigated (S12), and thereafter, the design is visualized so that the design can be outputted by the image output unit 1 (S13). Next, with the design evaluation method, the design quality is evaluated (S14), and if the evaluation result is good (S15), the process is shifted to a design and manufacturing phase of the goods using the design (S16), and the produced goods are sold (S17). In addition, at the step S15, if the evaluation result of the design is not good, the steps S12 to S15 are repeated until a good result is obtained.

In this manner, according to the goods design method, arbitrary design to be evaluated in regard to the design quality is imaged, and evaluation on the basis of brain wave reactions of the test subject 1b is performed with the design evaluation method about the design visualized. Further, until a good evaluation result is obtained, the process from the investigation of the design to the evaluation is repeated. Hence, it is possible to decide the final design of the goods on the basis of a highly reliable evaluation result without any subjective judgment based on the knowledge and experience of the test subject 1b, and therefore, it is possible to produce goods having a high probability of obtaining good sales. In this case, by performing the evaluation measurement for a plurality of test subjects, it is possible to enhance the reliability of the design evaluation.

In addition, because the design of an evaluation object is outputted as the image 1a by the image output unit 1, by virtually producing the image 1a by using computer graphics, it is possible to rightly decide the design even in a development phase, where a real object of a product does not exist, without producing any three-dimensional model.

In addition, the design evaluation method according to the above mentioned embodiment is not limited to vehicles such as automobiles or motorcycles, but, can be used for, for example, the design evaluation of products in every sector such as other industrial products such as aircrafts, ships, or various types of home electric appliances naturally, and clothes, toys, or craftworks.

In addition, in the above described embodiment, the evaluation measurement is performed for what the design of a goods before manufacturing is virtually expressed. Nevertheless, for example, by performing the design evaluation of the present invention for an article that has been already circulated in the market and obtains certain evaluation, it is also possible to forecast a real evaluation result of new design similar to the current design on the basis of relation between the evaluation result and real evaluation.

Moreover, also in a retail shop performing only sale of goods, by performing evaluation of, for example, a sample of new goods by using the design evaluation method before stocking the new goods from their manufacturer, it is possible to rightly perform the decision of the number of the stocked goods whose sales have been forecast.

What is claimed is:

1. A design evaluation method, comprising the steps of:

outputting an image, where design of an evaluated object is expressed, by predetermined image output means;

measuring brain waves of an arbitrary test subject while showing this image to the test subject;

comparing a pattern of a local distribution condition of a brain wave electric potential on the test subject's scalp with plural kinds of reference patterns set beforehand; and evaluating the design of the evaluated object by judging which of the plural kinds of reference patterns is similar to the pattern of the brain wave electric potential measured.

2. The design evaluation method according to claim 1, wherein the design of the evaluated object is evaluated on the basis of a brain wave reaction of a test subject in a predetermined scene of the image.

3. The design evaluation method according to claim 1, wherein images including scenes where the evaluated object is expressed from various angles are used.

4. The design evaluation method according to claim 1, wherein images including scenes where dynamic changes of the evaluated object are expressed are used.

5. The design evaluation method according to claim 1, wherein images including scenes where the evaluated objected is expressed with predetermined backgrounds are used.

6. The design evaluation method according to claim 1, wherein images including scenes where the evaluated object is expressed with another article or persons are used.

7. The design evaluation method according to claim 1, wherein the image is created by using computer graphics.

8. A goods design method for deciding design of goods before shifting to a design and manufacturing phase of the goods, comprising the steps of:

visualizing concrete design, which is to be evaluated on design quality, in an output-enabled condition by predetermined image outputter;

outputting this image by the image outputter and measuring brain waves of an arbitrary test subject while showing the image to the arbitrary test subject; and comparing a pattern of a local distribution condition of a brain wave electric potential on a test subject's scalp with plural kinds of reference patterns set beforehand; and evaluating the design quality by judging which of the reference patterns is similar to the pattern of the brain wave electric potential measured, wherein each of the steps is performed at least once on the basis of the evaluation result of the design.

9. The goods design method according to claim 8, wherein the image is produced by using computer graphics.

10. The goods design method according to claim 9, wherein an evaluated object whose real object does not exist is expressed in the image.

11. The goods design method according to claim 10, wherein the evaluated object is a vehicle.

* * * * *